United States Patent
Ruismäki

Patent Number: 5,526,818
Date of Patent: Jun. 18, 1996

[54] GAS COLLECTING UNIT

[75] Inventor: Pertti Ruismäki, Helsinki, Finland

[73] Assignee: Instrumentarium Corporation, Finland

[21] Appl. No.: 192,050

[22] Filed: Feb. 4, 1994

[30] Foreign Application Priority Data

Feb. 5, 1993 [FI] Finland ................................ 930522

[51] Int. Cl.⁶ .................................................. A61B 5/097
[52] U.S. Cl. ..................... 128/719; 128/730; 128/201.23
[58] Field of Search ..................................... 128/719, 730, 128/201.22, 202.12, 205.26, 201.23, 201.25, 205.25; 600/21, 22

[56] References Cited

U.S. PATENT DOCUMENTS

| | | |
|---|---|---|
| 2,418,473 | 4/1947 | Lambertsen et al. . |
| 3,744,491 | 7/1973 | Fischer . |
| 4,407,280 | 10/1983 | Trammell et al. ........... 128/205.26 |
| 4,589,408 | 5/1986 | Singer ........................ 128/201.25 |
| 4,637,383 | 1/1987 | Lopez ......................... 128/201.25 |
| 4,763,664 | 8/1988 | Meriläinen ..................... 128/719 |
| 4,856,531 | 8/1989 | Meriläinen . |
| 4,889,113 | 12/1989 | Pelloux-Gervais et al. ...... 128/201.25 |
| 5,335,653 | 8/1994 | Blomqvist et al. . |

FOREIGN PATENT DOCUMENTS

| | | |
|---|---|---|
| 2198760 | 4/1974 | France . |
| 3536519 | 4/1987 | Germany . |
| 51303 | 11/1988 | Germany . |
| 2188236 | 9/1987 | United Kingdom . |

*Primary Examiner*—Lee S. Cohen
*Attorney, Agent, or Firm*—Andrus, Sceales, Starke & Sawall

[57] ABSTRACT

A gas collecting unit (8) suitable for the examination of a patient's respiratory gas, which gas collecting unit is supplied from one or a plurality of gas sources (1) with a gas to be respired by a patient, and which gas collecting unit is used for delivering a gas, which at least partially contains a gas expired by a patient, to a measuring device (13) for examination. The gas collecting unit (8) comprises a dome (15) having a shell (17) which at least partially encloses a gas space (18) and which dome includes an opening (19) for pushing the head of a patient therethrough at least partially into the gas space (18) within the dome. A collar (16) has a wall (20) which extends around the dome opening (19) and which collar includes a neck opening (22) surrounded by the wall (20) for introducing the head of a patient therethrough towards the gas space (18). The wall (20) of said collar connects the shell of said dome (15) against the skin of a patient. The wall (20) surrounding the neck opening (22) of the collar is at least partially made of an elastic material.

15 Claims, 1 Drawing Sheet

GAS COLLECTING UNIT

BACKGROUND OF THE INVENTION

The present invention relates to a gas collecting unit suitable for the examination of a patient's respiratory gas and supplied from one or a plurality of gas sources with a gas to be respired by a patient, and which gas collecting unit is used for delivering a gas, which at least partially contains a gas expired by a patient, to a measuring device for examination, said gas collecting unit comprising a dome having a shell which at least partially encloses a gas space and which dome includes an opening for pushing the head of a patient therethrough at least partially into the gas space within the dome, and a collar having a wall which extends around the dome opening and which collar includes a wall-surrounded neck opening for introducing the head of a patient therethrough towards the gas space and the wall of said collar connecting the dome shell against the skin of a patient, and the gas collecting unit consisting of said collar and dome separating the surrounding gas space from that remaining inside.

In a variety of medical measurement and treatment procedures, the gas respired or intended to be respired by a patient must be isolated from the ambient air. A reason may be, for example, that a gas received by a patient for respiration must have a composition that differs from ambient air in a desired fashion. Another reason may be the need of measuring the concentrations of a gas respired by a patient, in which case the mixing of ambient air with the respiratory gas would produce a measuring error. Another possible reason is that the gas respired or intended to be respired by a patient could, upon seeping into the ambient air, produce a hazard to others in the room or extra costs as a result of wasting expensive gas.

There are several ways of preventing the mixing of a gas respired by a patient and the ambient air. One possibility is the isolation of a patient in a space totally sealed from ambient air and containing a gas with a controllable composition. Another possibility is to use a mask which seals against the face of a patient, covers the mouth and nose and through which the patient breaths.

Drawbacks encountered in the former method include e.g. the large size of a required apparatus and the resulting expensive price and complicated operation. Also, various procedures on a patient may become impossible or more difficult to perform with a patient in a totally isolated space. On the other hand, the latter method is not suitable for long-term use since, in order to retain its tightness, a mask requires continuous pressing against the face, which might cause blood circulation problems or even damage to the face. It is also true that a conscious patient may find a mask unpleasant and injuries possibly existing in the face can prevent the use of a mask.

A third method can be considered as an intermediary between those described above with just part of a patient, generally the head, being isolated from ambient air. This is usually done by closing the head of a patient in a gastight chamber. One example of such a case is a gas collecting unit for a metabolic measuring apparatus described in U.S. Pat. No. 4,763,664. A gas collecting unit is often referred to as a canopy. A problem in this type of equipment may be the sealing against the skin of a patient at the opening used for passing the head or upper body of a patient into the canopy. This opening need not be completely sealed provided that the examination or treatment procedure in question allows for a leak in either direction. However, there are such methods existing and in use, wherein a leak is not acceptable or it should be as negligible as possible.

In several devices, wherein it has been considered necessary to enclose the head of a patient within a gastight gas collecting unit, the sealing against the neck is effected by compression. Thus, the gas collecting unit is provided with a neck opening which is larger than the neck in its inoperative condition and upon sealing it is compressed to a smaller diameter and as tightly as possible against the neck. A result of this is that the rim of the opening may be left with tightness-affecting creases upon decreasing the circumference of the opening. Also, the required compressive force may be sufficiently strong to interfere with the circulation and even respiration of a patient. Furthermore, the mechanical design of such sealings based on reducing the size of a neck opening can be quite complicated.

SUMMARY OF THE INVENTION

An object of this invention is to eliminate the above problems. An object is to provide a gas collecting unit which seals against the skin of a patient as effectively as possible. Another object is to provide a gas collecting unit which is as tightly sealed as possible yet as pleasant as possible for a patient in operation. A further object is to provide a gas collecting unit whose fitting around the head of a patient is a simple procedure. A still further object is to provide a gas collecting unit which is structurally as simple as possible. Yet another object is to provide an economically priced gas collecting unit.

The characterizing features of a gas collecting unit of the invention are set forth in the annexed claims.

The invention relates to a gas collecting unit which separates a surrounding gas space from that remaining inside the gas collecting unit, a patient breathing the gas contained in said gas collecting unit. The principal components of a gas collecting unit include a dome and a collar. The dome is a self-sustaining component which is preferably capable of retaining the shape of a gas collecting unit, such that a shell insulating a gas space remaining inside the gas collecting unit from a surrounding gas space remains out of contact with the airways of a patient. Thus, the dome may comprise an abutment ring and an essentially gas-impermeable shell or, preferably, the dome comprises a shell which in itself is both a self-sustaining component and essentially impervious to gas. The dome should have such a shape that inside its shell remains a gas space which is nevertheless open in at least one direction for facilitating at least a partial introduction of the head of a patient into the gas space remaining inside the shell. Most preferably, the dome has the shape close to a semi-ellipsoid, as described in U.S. Pat. No. 4,763,664. A particularly suitable material for the dome is plastics, which in the most preferred case is even transparent for a patient to see what is happening around and, on the other hand, for the attending staff to observe the face of a patient. Another advantage offered by a dome which is a self-sustaining component can be considered to be the fact that it can be readily fitted with tubes for delivering a gas into and out of the dome.

The invention relates particularly to a collar included in a gas collecting unit and in turn usually mounted on the dome in a gastight fashion. Thus, the collar is a sort of extension for the dome intended for serving as a sealing means between the dome and the skin of a patient, whereby the flow of gas from a surrounding gas space into or out of the gas collecting unit therethrough is as negligible as possible. The collar is used for introducing the head of a patient therethrough into the gas collecting unit. Thus, the collar must be capable of sealing against the skin of a patient. Therefore, at least the wall of the collar surrounding a neck opening should be elastic whereby, prior to the introduction of a patient's head, the neck opening of the collar is stretched or extended to facilitate the introduction of a patient's head through the resulting opening. When the gas collecting unit has been successfully brought around a patient's head and the application of a force stretching the neck opening is released, the collar walls surrounding the neck opening, due to the elasticity thereof, have a tendency to return towards the former condition and to squeeze against the skin of a patient. The neck opening of the collar tends to squeeze e.g. around the neck of a patient or, if desired, even around the thorax. In order to keep a patient comfortable it would be desirable to have the neck-opening surrounding walls of the collar squeeze against the skin of a patient just sufficiently to attain gas tightness but not to interfere particularly with the subcutaneous circulation or respiration of a patient. This is achieved by the appropriate selection of a material for the collar and the thickness for a material used. The thicker a material being used, the stronger is the compressive force when the material is otherwise the same.

In order to achieve a good tightness, the neck opening of the collar with the collar in untensioned condition should have a circumference which is less than the circumference of the part of a patient's body around which the neck-opening surrounding wall of the collar is intended to squeeze.

Most commonly, the dome and the collar are separate components. In its simplest form the collar could be e.g. an annular object provided with a central neck opening for threading the head of a patient therethrough, the outer edge of said collar being fastened to the edges of an opening included in the dome. However, the collar has preferably a bag-like shape usually provided with two openings, at least one of such openings being surrounded by an elastic wall and said openings being connected by a void surrounded by the wall. In that case, one of the openings is a neck opening for introducing the head of a patient towards the dome therethrough. A wall surrounding the remaining opening is suitable for mounting around the edges of an opening included in the dome e.g. by stretching the opening provided, however, that this opening is also surrounded by an elastic wall. Thus, the edges of an opening included in the dome are preferably designed in a manner such that the collar opening fastens tightly to it due to the action of its tensile stress.

DESCRIPTION OF THE DRAWINGS

The invention will now be described in more detail with reference made to the accompanying patent drawings, in which.

DESCRIPTION OF THE PREFERRED EMBODIMENTS

Figure 1:
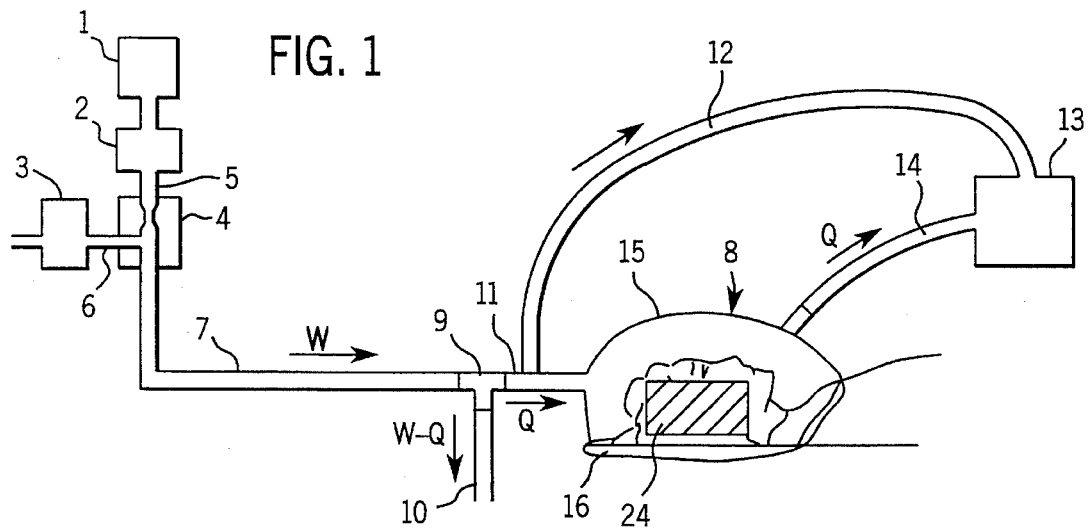
FIG. 1 is a schematic general view of one possible operating environment for using a gas collecting unit of the invention.

FIG. 1 illustrates the use of a gas collecting unit in one possible operating environment, wherein a patient is supplied with a gas containing more oxygen than the ambient air. A gas coming from a gas source 1, which in this preferred exemplary embodiment contains oxygen, is mixed with another gas, which in this case is air. The air can be drawn even from the space a patient is located in, i.e. often from the same room which hence serves also as a gas source. The regulation of the total flow and mixing ratio of oxygen and air to a patient is effected by means of flow controlling elements 2 and 3, which are preferably needle valves. These two flows are delivered to a patient preferably through a pneumatic element 4, the mixing of gases occurring therein. One example of a pneumatic element is an ejector which receives its driving force from the gas source 1. An oxygen jet arriving from the gas source along a conduit 5 produces a vacuum within the pneumatic element for sucking ambient indoor air from a conduit 6 to mix with the oxygen gas. The gas mixture flows along a conduit 7 towards a gas collecting unit 8, the head of a patient being shown thereinside.

Upstream of the gas collecting unit, some of the flow coming from flow controlling elements 2 and 3 is preferably deflected past the gas collecting unit. In order to direct the gas flow both into and past the gas collecting unit, the figure includes a branch-T fitting 9 fitted with a conduit 10 for a by-pass flow. This conduit 10 has a volume which is preferably at least equal to the single respiratory volume of a patient with no undesired outside gas capable of invading the gas collecting unit along conduit 10 at the time of reversal of a patient's respiration. Even more preferably, the volume of conduit 10 exceeds the maximum single volume of respiration. In practice, the single volume is often approximately 0,5–1 liters.

From the branch-T fitting to gas collecting unit 8 extends a conduit 11. A substantially lesser portion of the flow coming from flow controlling elements 2 and 3 is carried along conduit 10 past the gas collecting unit and, thus, a larger portion of the flow proceeds along conduit 11 to the gas collecting unit. A sample of the oxygen content of a gas advancing to the gas collecting unit is delivered along a conduit 12 to a measuring device 13. Preferably to the same measuring device 13 is also delivered from the gas collecting unit a gas to be examined along a conduit 14. Thus, the measuring device can be preferably used not only for the examination of the oxygen content of a gas but also its carbon dioxide content. The measuring device can be e.g. an apparatus described e.g. in U.S. Pat. No. 4,856,531 and manufactured under the tradename Deltatrac by Datex group, Instrumentarium Oy.

Figure 2:
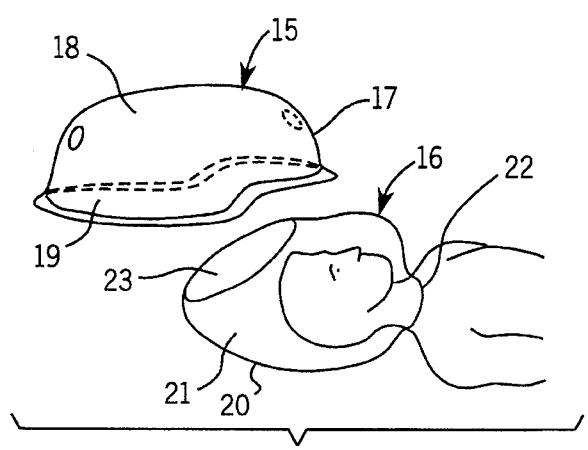
FIG. 2 is an exploded view of one preferred gas collecting unit of the invention.

The gas collecting unit 8 comprises a dome 15 and a collar 16. In FIG. 2, the collar 16 is unfastened from the dome 15. The dome comprises a shell 17 which partially encloses a gas space 18 providing, however, the shell with an opening 19 for introducing the head of a patient at least partially into said gas space 18 enclosed by the shell.

Figure 3:
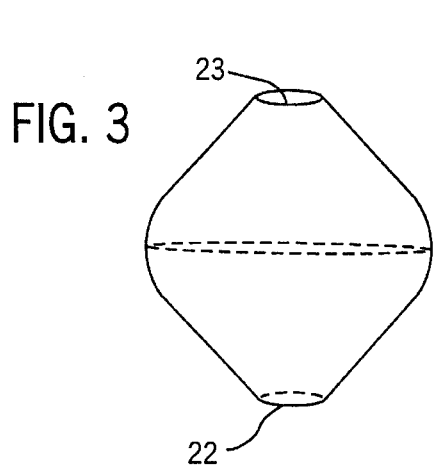
FIG. 3 shows a component included in the gas collecting unit depicted in FIG. 2.

The dome is preferably self-sustaining and possibly made of transparent plastics and fitted with a collar 16 as tightly as possible for eliminating gas leaks. Generally, the sealing is effected around the neck of a patient, as indicated in FIGS. 2 and 3, but just as well the sealing could be effected at the shoulders or abdomen. The collar extends preferably down below a patient's head as the patient is lying on his or her back in bed. This type of gas collecting unit is simple to install around the head of a patient.

FIGS. 2 and 3 illustrate in more detail one preferred collar of the invention. The collar includes a wall 20 with a void 21 thereinside. The wall is preferably like a film and, thus, with the collar in an unsupported state, the void-surrounding wall may collapse closely together. Preferably, the wall should be made of a material which is at least essentially impervious to gas. The wall 20 is provided with a neck opening 22 for introducing the head of a patient into the gas collecting unit 8 through said void 21 surrounded by the collar wall. The void wall surrounding said neck opening 22 must be elastic in order to be stretched at least to the extent that the head of a patient can be introduced therethrough whereafter, as the stretching is concluded, the wall around said opening tends to return towards its unstressed condition urging to seal itself against the skin of a patient. By virtue of the elasticity of the collar, such stretching can be simply and readily performed manually and, on the other hand, the tightening occurs with no creases or wrinkles and, thus, there will be no particular gas leaks. In this case, the entire collar wall need not be made of an elastic material but it is sufficient that the wall surrounding the neck opening be capable of adequate elastic action. In that case, the remaining collar should preferably be made of a flexible material. However, it is preferred that the entire collar be made of the same elastic material.

The collar shown in FIGS. 2 and 3 further includes another opening 23 intended for fastening the collar to said dome 15. The engagement of collar and dome can be effected e.g. by stretching the opening sufficiently for bringing it over the dome rim, whereafter the collar tends to return towards its original condition upon the conclusion of stretching by pressing against the dome rim. A condition for such a preferred coupling solution is of course that the walls surrounding this latter opening are also made of an elastic material. The coupling of collar and dome in a gastight fashion can also be effected in another way. Particularly in the case that the wall surrounding this opening is not made of an elastic material but e.g. of a flexible material instead, the fastening can be effected e.g. by gluing or some other suitable means.

Thus, a gas collecting unit of the invention is particularly suitable for such a solution that a patient is only intended to be partially closed within the gas collecting unit.

At least the wall surrounding said neck opening 22 included in the collar for introducing the head of a patient into a gas collecting unit is made of an elastic material, e.g. rubber. A particularly suitable material for this purpose is latex rubber. A suitable thickness for the wall surrounding one or a plurality of openings included in a rubber-made collar is about 0,5 mm or less. The most preferred thickness is about 0,25 mm or less. It should have an extensibility of at least 100% for increasing the opening diameter as a result of the extension to at least double. Preferably, the extensibility is 200% or more. Most preferably, the extensibility is 600% or more. What is the sufficient extensibility for a rubber film included in the collar depends essentially on which part of a patient's body the neck opening 22 included therein is intended to be sealed against. If the opening is to be sealed e.g. on the neck of a patient, the wall must be more extensible than in the case that said opening 22 would be sealed or tightened at the shoulder level. In the former case, the opening received against the skin of a patient's neck must have a circumference which, in the unextended state, is less than the circumference of a patient's neck. In order to introduce the head of a patient through said opening 22, the opening should be stretched or extended considerably due to the fact that the head has a circumference which exceeds that of the neck. On the other hand, for example at the shoulder level the circumference exceeds that of the head and, thus, the circumference of opening 22, with the collar in an unextended state, can already be closer to the dimensions of the shoulders, whereby the opening need not be stretched very extensively prior to placing it in position.

The collar shown in FIG. 3 is of a preferred design since downstream of opening 22, with the collar in an unextended state, the circumference of the inner collar surface increases when moving away from this opening towards the other end of said collar if the circumference is measured in the direction parallel to the edges of the opening. In this preferred embodiment, as both ends of the collar are provided with openings, the circumference of the inner collar surface increases from both openings towards the midway point of the collar at which the circumference of the inner surface is at its maximum, when the circumference is measured in the direction parallel to the edges of the nearest opening and when the collar is in an unextended state. Thus, the increase of circumference may continue e.g. up to the midway point of a collar and thereafter it may decrease towards the opening at the other end of a collar. This type of solution offers a benefit that, if necessary, one or both of the openings can be enlarged by simply cutting off a piece of the end of a collar e.g. in the direction of such opening. An adjustment of the size of an opening may be necessary as patients have necks of varying thicknesses or if the objective is to make a collar airtight at the level of a patient's shoulders instead of his or her neck or even if a collar is to be fitted with domes of varying sizes. Furthermore, this type of a collar with a wider mid-section is comfortable from the viewpoint of a patient by affording freedom of movement, since a loose collar wall does not tighten as a patient moves and, thus, does not produce an adverse leak with the neck opening stretching to exceed the size of the neck.

The collar could be designed for example to be spherically circular but preferably in its inoperative condition, as seen from one direction, it is flat and, when rotated through 90°, it is roundish as shown in FIG. 3. The difference with respect to a spherical shape is that a spherical collar would urge itself in its inoperative condition towards a cup-like shape while this strives towards a flat shape. The advantage gained by a flat shape is that, upon placing it in a cutter, the collar does not develop creases which are very likely to occur when cutting an entirely spherical collar. The creases would result in an uneven cut-off edge which might lead to the rupture of a collar upon stretching the opening.

FIG. 1 illustrates yet another preferred detail associated with the gas collecting unit 8. This relates to a pressure-difference detecting element 24 for indicating a pressure difference existing between gas collecting unit 8 and its ambient conditions. Said element 24 is in a flow communication both with a gas space existing inside the gas collecting unit, which gas a patient breaths, and with a gas space outside the gas collecting unit, to which the pressure existing inside is desired to be compared. This pressure-difference detecting element can be used for adjusting the internal respiratory gas pressure inside the gas collecting unit to a desired level whenever necessary.

The invention is by no means limited to the above embodiments but various details of the invention can be modified within the scope of the claims. The use of a gas collecting unit is not restricted exclusively to the operating environment shown in FIG. 1.

FIGS. 2 and 3 illustrate a collar provided at both ends with openings when the dome and the collar are separated from each other. However, the collar may only be provided with one opening or just a neck opening, whereby the collar could resemble e.g. a bag. In this case, a dome could be inserted within the collar through the same neck opening as the head of a patient.

Furthermore, the collar illustrated in the figures includes a void 21 surrounded by a wall, which is not necessary either, although useful. What is essential in view of the invention is that a wall surrounding the neck opening is at least partially made of an elastic material.

I claim:

1. A gas collecting unit (8) suitable for collecting the respired gases of a patient for delivery to a measuring unit, said gas collecting unit comprising:

a dome (15) having a shell (17) defining a space in which the head of the patient may be positioned, said dome having means for providing the respired gas of the patient for delivery to the measuring unit, said dome having an opening (19) by which the dome may be placed over the head and neck of the patient to position the head of the patient in said space; and collar means (16) for sealing said space defined by said shell of said dome, said collar means having a generally tubular wall (20) with first and second ends, said collar means being joinable to said dome so that the tubular wall of said collar means extends around the periphery of said opening, said collar means having an opening (22) at said first of said ends by which said first end embraces a selected portion of the patient's body when the head of the patient is positioned in said space, at least the portion of said tubular wall adjacent said opening at said first end of said collar means being formed of an elastic material capable of assuming a stretched state and a relaxed state, said opening at said first end of said collar means being smaller in size that said selected portion of the patient's body when said elastic material is in the relaxed state, said elastic material of said tubular wall adjacent said first end of said collar means being stretched to permit said opening at said first end of said collar means to embrace said selected portion of the patient's body and thereafter allowed to relax into contiguity with said body portion, said collar means having an opening (23) at said second end, said second end of said collar means being joined to said dome so that the portion of said tubular wall adjacent said opening in said second end of said collar means extends sealingly around the periphery of said opening of said dome, said portion of said tubular wall adjacent said opening in said second end of said collar means being formed of an elastic material, so that said opening of said second end of said collar means may be stretched to extend around said periphery of said opening of said dome and thereafter allowed to relax;

the extension of the wall around the periphery of said opening of said dome and the embracing of the selected portion of the patient's body by said first end of said tubular wall sealing said space from an ambient environment for the gas collecting unit.

2. A gas collecting unit according to claim 1 wherein said dome has a protruding rim on the periphery of said opening and wherein said opening of said second end of said collar means is stretched over said rim and thereafter allowed to relax to seal said space.

3. A gas collecting unit as set forth in claim 1 wherein said tubular wall is formed of an elastic material.

4. A gas collecting unit as set forth in claim 1 wherein said tubular wall has a longitudinal axis extending between said first and second ends, wherein said first end of said tubular wall has a given inner circumference, wherein said second end of said tubular wall has a given inner diameter, and wherein the inner circumference of said tubular wall increases as the distance along said longitudinal axis from each of said first end and said second end increases.

5. A gas collecting unit as set forth in claim 4 wherein said tubular wall has a maximum inner diameter approximately midway along said longitudinal axis between said first and second ends.

6. A gas collecting unit (8) suitable for collecting the respired gases of a patient for delivery to a measuring unit, said gas collecting unit comprising:

a dome (15) having a shell (17) defining a space in which the head of the patient may be positioned, said dome having means for providing the respired gas of the patient for delivery to the measuring unit, said dome having an opening (19) by which the dome may be placed over the head and neck of the patient to position the head of the patient in said space; and collar means (16) for sealing said space defined by said shell of said dome, said collar means having a generally tubular wall (20) with first and second ends, said collar means being joinable to said dome so that the tubular wall of said collar means extends around the periphery of said opening, said collar means having an opening (22) at said first of said ends by which said first end embraces a selected portion of the patient's body when the head of the patient is positioned in said space, at least the portion of said tubular wall adjacent said opening at said first end of said collar means being formed of an elastic material capable of assuming a stretched state and a relaxed state, said opening at first end of said collar means being smaller in size that said selected portion of the patient's body when said elastic material is in the relaxed state, said elastic material of said tubular wall adjacent said first end of said collar means being stretched to permit said opening at first end of said collar means to embrace said selected portion of the patient's body and thereafter allowed to relax into contiguity with said body portion, said tubular wall having a longitudinal axis extending between said first and second ends, wherein said first end of said tubular wall has a given inner circumference and wherein the inner circumference of said tubular wall increases as the distance along said longitudinal axis from said first end increases;

the extension of the wall around the periphery of said opening of said dome and the embracing of the selected portion of the patient's body by said first end of said tubular wall sealing said space from an ambient environment for the gas collecting unit.

7. A gas collecting unit as set forth in claim 6 wherein said collar means is further defined as having an opening at said first end by which said first end embraces the neck of the patient.

8. A gas collecting unit as set forth in claim 6 wherein said tubular wall is formed of an elastic material.

9. A gas collecting unit as set forth in claim 6 wherein said portion of said tubular wall adjacent said opening at said first end is formed of an elastic material which exhibits an amount of permanent deformation upon relaxation following stretching that allows said first end of said tubular wall to embrace the selected portion of the patient's body with the desired amount of circumferential tension about said opening.

10. A gas collecting unit as set forth in claim 6 wherein at least said portion of said tubular wall adjacent said opening at said first end is formed of an elastic material capable of increasing the size of said opening to at least double the size of said opening when said elastic material is in the relaxed state.

11. A gas collecting unit as set forth in claim 10 wherein at least said portion of said tubular wall adjacent said opening at said first end is formed of an elastic material capable of increasing the size of said opening by at least 200% over the size of said opening when said elastic material is in the relaxed state.

12. A gas collecting unit as set forth in claim 6 wherein the tubular wall (20) adjacent the opening (22) of said collar means at said first end has a thickness of less than 0.5 mm.

13. A gas collecting unit as set forth in claim 12 wherein the tubular wall (20) adjacent the opening (22) of said collar means at said first end has a thickness of less than 0.25 mm.

14. A gas collecting unit as set forth in claim 6 wherein the tubular wall (20) adjacent the opening (22) of said collar means at said first end is made of rubber.

15. A gas collecting unit according to claim 6 wherein said tubular wall has a maximum inner diameter approximately midway along said longitudinal axis between said ends.

* * * * *